(12) United States Patent
Blancke et al.

(10) Patent No.: US 10,525,204 B2
(45) Date of Patent: Jan. 7, 2020

(54) DRUG DELIVERY DEVICE

(71) Applicant: Sanofi-Aventis Deutschland GmbH, Frankfurt am Main (DE)

(72) Inventors: Stefan Blancke, Frankfurt am Main (DE); Axel Teucher, Frankfurt am Main (DE); Michael Jugl, Frankfurt am Main (DE); Christiane Schneider, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 542 days.

(21) Appl. No.: 15/037,338

(22) PCT Filed: Nov. 17, 2014

(86) PCT No.: PCT/EP2014/074706
§ 371 (c)(1),
(2) Date: May 18, 2016

(87) PCT Pub. No.: WO2015/074981
PCT Pub. Date: May 28, 2015

(65) Prior Publication Data
US 2016/0296709 A1    Oct. 13, 2016

Related U.S. Application Data

(60) Provisional application No. 61/907,577, filed on Nov. 22, 2013.

(30) Foreign Application Priority Data

Apr. 24, 2014 (EP) .................................... 14165750

(51) Int. Cl.
*A61M 5/315* (2006.01)
*A61M 5/24* (2006.01)
*A61M 5/31* (2006.01)

(52) U.S. Cl.
CPC .......... *A61M 5/31535* (2013.01); *A61M 5/24* (2013.01); *A61M 5/3158* (2013.01);
(Continued)

(58) Field of Classification Search
CPC ................ A61M 5/31535; A61M 5/24; A61M 5/31505; A61M 5/31551; A61M 5/3158; A61M 5/3146
See application file for complete search history.

(56) References Cited

U.S. PATENT DOCUMENTS 533,575 A * 2/1895 Wilkens ................. A61C 1/141
433/127
5,127,906 A * 7/1992 Landry, Jr. .......... A61M 5/31511
604/110
(Continued)

FOREIGN PATENT DOCUMENTS

CN    1835774    9/2006
EP    0937471 A2    8/1999
(Continued)

OTHER PUBLICATIONS

International Search Report in International Application No. PCT/EP2014/074706, dated Oct. 7, 2015, 10 pages.
(Continued)

*Primary Examiner* — Jenna Zhang
(74) *Attorney, Agent, or Firm* — Fish & Richardson P.C.

(57) ABSTRACT

The present disclosure provides for a drive assembly for a drug delivery device. The drive assembly comprises a housing; a piston rod having a longitudinal axis, a distal end and a proximal end and being axially movable in a distal direction relative to the housing and a mid-body axially fixed inside of the housing and coupled to the piston rod. The mid-body comprises at least one metal ratchet arm configured to prevent the piston rod from moving in the proximal (Continued)

direction. Moreover, a drug delivery device with such a drive assembly is presented.

16 Claims, 4 Drawing Sheets

(52) U.S. Cl.
CPC .... *A61M 5/31505* (2013.01); *A61M 5/31551* (2013.01); *A61M 5/3146* (2013.01)

(56) References Cited

U.S. PATENT DOCUMENTS

| | | | | |
|---|---|---|---|---|
| 5,226,895 | A * | 7/1993 | Harris | A61J 1/1406 604/208 |
| 5,279,586 | A * | 1/1994 | Balkwill | A61M 5/3158 222/309 |
| 5,304,152 | A * | 4/1994 | Sams | A61M 5/31553 604/207 |
| 5,320,609 | A * | 6/1994 | Haber | A61M 5/2033 604/135 |
| 5,383,865 | A * | 1/1995 | Michel | A61M 5/31553 604/186 |
| 5,480,387 | A * | 1/1996 | Gabriel | A61M 5/20 604/134 |
| 5,505,704 | A * | 4/1996 | Pawelka | A61M 5/19 604/191 |
| 5,582,598 | A * | 12/1996 | Chanoch | A61M 5/31551 222/309 |
| 5,626,566 | A * | 5/1997 | Petersen | A61M 5/31551 222/309 |
| 5,674,204 | A * | 10/1997 | Chanoch | A61M 5/31535 604/207 |
| 5,688,251 | A * | 11/1997 | Chanoch | A61M 5/3146 222/309 |
| 5,921,966 | A * | 7/1999 | Bendek | A61M 5/24 604/207 |
| 5,961,495 | A * | 10/1999 | Walters | A61M 5/31553 604/111 |
| 6,004,297 | A * | 12/1999 | Steenfeldt-Jensen | A61M 5/31551 604/207 |
| 6,193,698 | B1 * | 2/2001 | Kirchhofer | A61M 5/31551 604/207 |
| 6,221,046 | B1 * | 4/2001 | Burroughs | A61M 5/31551 604/153 |
| 6,235,004 | B1 | 5/2001 | Steenfeldt-Jensen et al. | |
| 6,248,095 | B1 * | 6/2001 | Giambattista | A61M 5/31551 604/207 |
| 6,899,698 | B2 | 5/2005 | Sams | |
| 6,936,032 | B1 * | 8/2005 | Bush, Jr. | A61M 5/31551 604/187 |
| 7,241,278 | B2 | 7/2007 | Moller | |
| 7,291,132 | B2 * | 11/2007 | DeRuntz | A61M 5/31551 604/207 |
| 7,427,275 | B2 * | 9/2008 | DeRuntz | A61M 5/31551 604/207 |
| 9,533,104 | B2 * | 1/2017 | Raab | A61M 5/31555 |
| 2002/0052578 | A1 * | 5/2002 | Moller | A61M 5/24 604/208 |
| 2002/0120235 | A1 * | 8/2002 | Enggaard | A61M 5/20 604/135 |
| 2003/0050609 | A1 * | 3/2003 | Sams | A61M 5/20 604/208 |
| 2004/0059299 | A1 | 3/2004 | Moller | |
| 2004/0210199 | A1 * | 10/2004 | Atterbury | A61M 5/31535 604/224 |
| 2004/0267207 | A1 * | 12/2004 | Veasey | A61M 5/24 604/208 |
| 2005/0113765 | A1 | 5/2005 | Veasey et al. | |
| 2006/0153693 | A1 * | 7/2006 | Fiechter | A61M 5/31553 417/63 |
| 2006/0206057 | A1 * | 9/2006 | DeRuntz | A61M 5/31551 604/224 |
| 2008/0027397 | A1 * | 1/2008 | DeRuntz | A61M 5/31551 604/220 |
| 2009/0275916 | A1 * | 11/2009 | Harms | A61M 5/24 604/506 |
| 2010/0137792 | A1 * | 6/2010 | Boyd | A61M 5/31555 604/68 |
| 2011/0046565 | A1 * | 2/2011 | Radmer | A61M 5/20 604/211 |
| 2011/0245780 | A1 * | 10/2011 | Helmer | A61M 5/31515 604/211 |
| 2013/0079727 | A1 * | 3/2013 | Schildt | A61M 5/24 604/207 |
| 2013/0226097 | A1 * | 8/2013 | Raab | A61M 5/31555 604/208 |
| 2014/0236097 | A1 * | 8/2014 | Jugl | A61M 5/31551 604/211 |
| 2015/0359970 | A1 * | 12/2015 | Jugl | A61M 5/31501 604/211 |
| 2016/0008550 | A1 * | 1/2016 | Jugl | A61M 5/31541 604/208 |
| 2016/0199585 | A1 * | 7/2016 | Jugl | A61M 5/31511 604/218 |
| 2016/0206824 | A1 * | 7/2016 | Jugl | A61M 5/31541 |
| 2016/0235926 | A1 * | 8/2016 | Blancke | A61M 5/24 |
| 2016/0235927 | A1 * | 8/2016 | Blancke | A61M 5/31533 |
| 2016/0263330 | A1 * | 9/2016 | Blancke | A61M 5/31533 |
| 2016/0279337 | A1 * | 9/2016 | Blancke | A61M 5/3155 |
| 2016/0287799 | A1 * | 10/2016 | Blancke | A61M 5/31543 |
| 2016/0287802 | A1 * | 10/2016 | Blancke | A61M 5/31551 |
| 2016/0296711 | A1 * | 10/2016 | Blancke | A61M 5/31551 |
| 2016/0317753 | A1 * | 11/2016 | Jugl | A61M 5/20 |
| 2016/0325049 | A1 * | 11/2016 | Jugl | A61M 5/31555 |

FOREIGN PATENT DOCUMENTS

| | | | |
|---|---|---|---|
| EP | 0937476 | A2 | 8/1999 |
| EP | 9938554 | A1 | 8/1999 |
| EP | 2438944 | A1 | 4/2012 |
| EP | 2452710 | A1 | 5/2012 |
| JP | H3-503608 | | 8/1991 |
| JP | 2006-519075 | | 8/2006 |
| JP | 2013-506442 | | 2/2013 |
| WO | 0110484 | A1 | 2/2001 |
| WO | WO 2004/078239 | | 9/2004 |
| WO | 2005018721 | A1 | 3/2005 |
| WO | 2010066796 | A1 | 6/2010 |
| WO | WO-2010112575 | A1 * | 10/2010 ............. A61M 5/24 |
| WO | 2011039202 | A1 | 4/2011 |
| WO | 2013156516 | A1 | 10/2013 |
| WO | WO 2013/156516 | | 10/2013 |

OTHER PUBLICATIONS

International Preliminary Report on Patentability in International PCT/EP2014/074706, dated May 24, 2016, 6 pages.

* cited by examiner

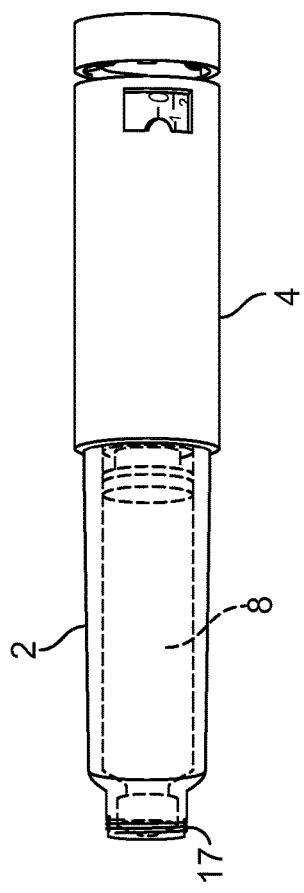
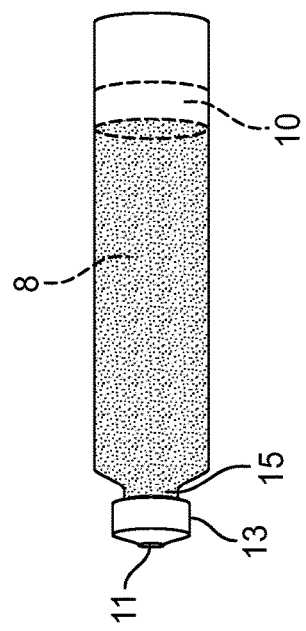
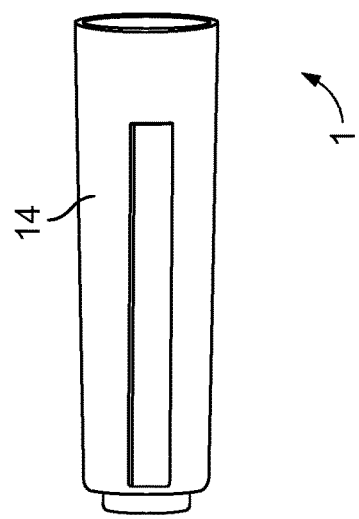
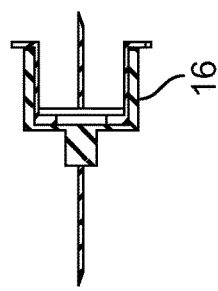
FIG. 1
FIG. 2

DRUG DELIVERY DEVICE

CROSS REFERENCE TO RELATED APPLICATIONS

The present application is a U.S. National Phase Application pursuant to 35 U.S.C. § 371 of International Application No. PCT/EP2014/074706 filed Nov. 17, 2014, which claims priority to U.S. Provisional Patent Application No. 61/907,577 filed Nov. 22, 2013 and European Patent Application No. 14165750.2 filed Apr. 24, 2014. The entire disclosure contents of these applications are herewith incorporated by reference into the present application.

FIELD OF INVENTION

The present disclosure is generally directed to pen-type injection devices and specifically to dose setting mechanisms for such drug delivery devices. Such devices provide for self-administration of medicinal product from a multi-dose cartridge and permit a user to set the delivery dose. The present application may find application in both disposable and reusable type drug delivery devices. However, aspects of the invention may be equally applicable in other scenarios as well.

BACKGROUND

Pen type drug delivery devices have application where regular injection by persons without formal medical training occurs. This is increasingly common among patients having diabetes where self-treatment enables such patients to conduct effective management of their disease. Diabetes has been shown to cause certain problems. For example, people with diabetes can get high blood pressure, kidney disease, nerve damage, heart disease, and even in certain circumstances blindness. The damage caused by these problems may occur in patients whose blood sugar has been out of control for years. Keeping blood sugar under control, by way of effective insulin administration, is one method that can help prevent this damage from occurring.

In addition, people with diabetes can go into "diabetic coma" if their blood sugar is too high. They can also develop blood sugar that is too low (i.e hypoglycemia) if they don't get enough food, or they exercise too much without adjusting insulin or food. Both diabetic coma and hypoglycemia can be very serious, and even fatal, if not treated quickly. Closely watching blood sugar, being aware of the early signs and symptoms of blood sugar that is too high or too low, and treating those conditions early can prevent these problems from becoming too serious.

Pen type drug delivery devices have been designed and developed to help patients suffering from diabetes and other disease states so as to prevent such problems from occurring. The circumstances identified above highlight a number of design considerations and criteria for drug delivery devices, especially those that may be used to treat diabetes. As just one example, one requirement is that the drug delivery device must be robust in construction. The drug delivery device must also be easy to use both in terms of the drug delivery device manipulation and understanding of the device's operation. Diabetics, for instance, have to inject themselves repeatedly with insulin solution and the volume of insulin to be injected may vary from patient to patient and even from injection to injection. For at least this reason, certain diabetics may require drug delivery devices that allow the patient to inject successive measured dosages of the same or perhaps different preset volumes of insulin solution accurately and with minimum dexterity challenges. This presents a further design challenge since, in the case of certain diabetics, users may have impaired vision and/or may be physically infirm with limited dexterity.

Generally, pen type injection devices include a cartridge having a slidable piston and containing a multi-dose quantity of liquid medication. A lead screw extending from the dose setting mechanism of the injector pen is movable in a forward (i.e., distal direction) to advance the piston within the cartridge in such a manner as to dispense the contained medication from an outlet at the opposite cartridge end, typically through a needle that penetrates a stopper or septum at that opposite end. In disposable or prefilled pens where the cartridge is permanently sealed within the pen housing, after a pen has been utilized to exhaust the supply of medication within the cartridge, the entire pen is then discarded. In reusable pens, after a pen has been utilized to exhaust the supply of medication within the cartridge, the pen is disassembled to allow replacement of the spent cartridge with a fresh cartridge, and then the pen is reassembled for its subsequent use.

A number of pen type injection devices are commercially available and unfortunately a number of those devices suffer from one or more design flaws that may result in the improper use of the injection device or the delivery of an inaccurate dosing of the medicament. Inaccurate dose setting could lead to fatal results. Other design flaws allow the possibility that a counterfeiter can dissemble a disposable pen and insert bogus medicament cartridge. This pen is then reassembled and sold as new. Such design flaws may not be realized when a pen is first commercialized and may only become apparent after the injection device has been in commercial use by patients for an extended period of time. As such, there exists a need to evaluate existing pen designs to identify the design flaws and then take corrective action, which typically would include redesigning certain original mechanisms within the injection device.

One such pen injector lending itself to design improvements is described in WO 2005/018721. The following describes a number of such design flaws and presents corrective solutions to eliminate these flaws.

SUMMARY

In most, if not all, pen injection type devices dose accuracy is significantly affected if the distal end of the lead screw, through the associated bearing, is not in continuous engagement with the proximal end or face of the cartridge piston prior to the user setting a dose. In other words, in some dosing mechanism designs there is one or more flaws that allows the lead screw to move or otherwise translate off the piston proximally after a dose is injected and before a subsequent dose is set. In these cases the bearing is no longer in contact with the proximal end of the piston thus creating a gap or void space between the distal face of the bearing and the proximal face of the piston. When a next dose is set and delivered, the lead screw would necessarily traverse this unintended gap before contacting and moving the piston. Because there is no movement of the piston during this gap closure, and hence no expulsion of medicament from the cartridge, the actual dose delivered will be less than that set by an amount directly proportional to the size of the gap. Accordingly, it is of prime importance to prevent any unintended proximal movement of the lead screw between dose delivery and the setting of the next dose.

A physical examination of the commercial pen injection device that is generally described in WO 2005/018721 or a pen injection device basing on a similar principle shows that a respective design provides a piston rod which could be a lead screw in particular, a dose knob, a so called number sleeve and a clutch component coupling the number sleeve with at least another component, namely a dial link that itself may—at least temporarily—act together with other driving means of the device, e.g. a so called drive nut, in order to set and deliver a predetermined dose of a medicament. When the piston rod is formed as a lead screw, the drive nut may be in a threaded connection with said lead screw. The clutch component may act so as to engage the dial link with the number sleeve in a first axial arrangement relative to each other and to disengage the dial link from the number sleeve in a second axial arrangement relative to each other.

The number sleeve and the dial link may be rotationally fixed to each other in the first axial arrangement, wherein a screwing motion of these two parts together by rotational movement of the dose knob may lead to a setting of a dose of a medicament. In the second axial arrangement, the dial link and the number sleeve are disengaged from each other such that the number sleeve may be rotationally movable with respect to the dial link in order to actuate the drive nut and hence the piston rod or lead screw for dispensing the set dose of the medicament out of the device.

An inconvenience of such a device is given by the fact that the piston rod or lead screw may be advanced in either the proximal or the distal direction, if a user pushes the dose knob in the distal direction and simultaneously rotates the dose knob in either direction (clockwise or counter clockwise).

For example, such a situation can develop as follows. The user begins to set a dose by rotating the dose knob causing the number sleeve to axially move in the proximal direction. Then, the user grips the number sleeve thereby preventing the number sleeve from further rotating and therefore from further moving in an axial direction. However, the user continues to rotate the dose knob while at the same time he pushes the dose knob axially in the distal direction towards an injection site. This causes said clutch component to disengage from the dial link thereby allowing relative rotation of the dial link and the number sleeve. As the pen injection device as explained above may be configured with the dose knob permanently attached to the dial link, rotation of the dose knob necessarily rotates the dial link. Since the dial link may be rotationally engaged with the drive nut as explained above, the drive nut may also rotate. Rotation of the drive nut while preventing the number sleeve, and hence the inner sleeve, from moving will cause the drive nut to rotate in a fixed axial position. Since consequently the drive nut is prevented from translating or screwing up/down along the lead screw, the lead screw, which is rotational fixed by a mid-body of the device, will be forced to translate axially relative to the threaded connection with the drive nut in either the distal or the proximal direction depending on which way the user turns the dose knob. If the lead screw translates distally, is it possible to push a cartridge piston distally causing unwanted expulsion of medicament from the cartridge. Alternatively, if the lead screw is caused to translate proximally, this proximal movement will cause a lead screw bearing to disengage from the proximal face of the cartridge piston creating an undesired gap that will lead to an inaccurate dose.

To solve these problems, the present invention generally provides a drive assembly according to claim 1 as well as a drug delivery device with such a drive assembly according to claim 13 which overcome the aforementioned deficiencies.

In particular, such a drive assembly comprises a housing, a piston rod having a longitudinal axis, a distal end and a proximal end and being axially movable in a distal direction relative to the housing, and a mid-body axially fixed inside of the housing and coupled to the piston rod. The mid-body comprises at least one metal ratchet arm configured to prevent the piston rod from moving in the proximal direction. The drive assembly has the advantage that any unwanted movement of the piston rod is inhibited.

The drive assembly and the respective drug delivery device of the present disclosure provide an anti-backup feature for the piston rod. In particular, the piston rod may provide a keyway configuration comprising a smooth surface that is engaged by a metal ratchet arm. The ratchet arm may preferably have an angled or wedge shaped distal end that claws or "digs into" the smooth surface of the keyway. In this way, the metal ratchet arm prevents the piston rod from moving in the proximal direction, such as during the situation described above. Preferably, one or more metal ratchet arms may be provided. In one preferred arrangement, the metal ratchet arm may comprise a separate metal spring. In an alternative arrangement, the metal ratchet arm may be molded into a mid body of a housing of the assembly. Alternatively, the ratchet arm may also be of plastic material or other synthetic material.

Moreover, according to an alternative embodiment, it is also conceivable that instead of a smooth surface of the keyway the piston rod comprises a roughened keyway with teeth for example that may interact with the metal ratchet arm in order to prevent a proximal movement of the piston rod.

The piston rod may be designed as a lead screw that is rotatably fixed during dose setting and dose delivery and that includes a threaded shaft.

Further herein, a method and system for proving a drug delivery device are provided. The device comprises a drug delivery device housing and a medicament contained in the drug delivery device housing. The drug delivery device further comprising a mid-body axially fixed inside of the housing. The mid-body comprising tabs that slidably fit within a keyway in a lead screw so as to prevent rotation of the lead screw within the housing. The mid-body further comprising at least one metal ratchet arm configured to prevent the lead screw from moving in the proximal direction.

Moreover, some embodiments are presented that modify the original design of dosing mechanism and drug delivery device as described in the WO 2005/018721 to prohibit this proximal motion of the lead screw.

In one arrangement, a modification is made to the mid-body structure. The existing design of the mid-body provides a central opening having an inward facing anti-rotation mechanism formed from a pair of diametrically opposed elements or tabs having squared off inward ends that each slidably fit within longitudinal flat or smooth keyways in the lead screw. At least one, preferably two metal ratchet arms projecting distally and slightly inwardly toward the longitudinal or centerline axis of the device may be added to the mid-body near the central opening of the mid-body. These metal ratchet arms may comprise separate components or may be molded directly into the mid-body. During dose delivery as the lead screw is pushed distally, the positioning of the distal end of the metal ratchet arms allow the smooth keyway surface of the lead screw to slide under the metal ratchet arms but only in the distal direction. As such, the ratchet arms are designed to by uni-directional, meaning that the distal ends of the ratchet arms claw or "dig-into" the smooth surface of the lead screw keyway so as to prevent proximal movement of the lead screw, thus keeping the lead screw bearing in contact with the proximal face of the cartridge piston.

The pen type delivery device drug including the above described design improvement includes a housing, a lead screw having a threaded shaft is rotatably fixed during dose setting and injecting that only moves axially in a distal direction relative to the housing during dose administration and is always prevented from moving proximally. The device also has a fluid container or cartridge defining a medicine-filled reservoir with a movable piston at one end and an outlet at the other end, where the piston is engaged by a bearing connected to the distal end of the lead screw. The piston is advanced toward the outlet or distal end of the cartridge when the lead screw is moved distally during dose administration.

A drive nut is threadedly engaged with the threads on the lead screw and can rotate and move proximally relative to the lead screw and housing during dose setting. A number sleeve is threadedly engaged with the housing and is screwed outwardly in the proximal direction relative to the housing during dose setting. A dial link is slidably and rotationally engaged with the drive nut and is axially movable and rotatably fixed relative to the drive nut. The dial link is rotatably fixed with the number sleeve through a clutch when the dial link and number sleeve are in a first axial arrangement and when in a second axial position the clutch, and hence the number sleeve, are disengaged from the dial link and the dial link becomes rotatable relative to the number sleeve. An inner sleeve is threadedly engaged with the number sleeve, were the inner sleeve is axially movable but rotatably fixed relative to the housing. During dose setting, the dial link and the number sleeve are in the first axial arrangement, whereby a screwing motion of the dose knob that is connected to the dial link and number sleeve relative to the housing screws the dial link and the number sleeve a first axial distance from a home position causing the number sleeve to extend in the proximal direction outwardly from the housing or body of the device. The screwing motion of the dial link screws the drive nut along the lead screw threaded shaft a second axial distance different than the first axial distance.

During dose dispensing, the dial link and the number sleeve element are in the second axial arrangement, whereby a screwing motion of the number sleeve relative to the housing back or inward toward the home position advances the inner sleeve without rotation in the distal direction to axially advance the drive nut and thereby the lead screw and the fluid container piston to dispense medicine from the outlet. The pen injector disclosed herein can be provided with a mechanical advantage that makes it easier for the user to push the dose knob during the dispensing of medication, which mechanical advantage can be very high and conveniently selected by the manufacturer during apparatus design. This mechanical advantage allows the number sleeve to travel a greater axial distance than the lead screw it advances, thus allowing for small doses to be delivered.

In the following an enumeration of advantageous aspects and embodiments of a device as presented herein is given:

1. A drug delivery device comprising:
   a housing;
   a lead screw having a longitudinal axis, a distal end and a proximal end that is rotatably fixed during dose setting and dose delivery and axially movable in a distal direction relative to the housing, the lead screw including a threaded shaft and a bearing foot connected to the distal end, wherein the lead screw has a smooth keyway positioned parallel to the longitudinal axis;
   a cartridge with a movable piston at one end and an outlet at the other end, the piston engagable by the lead screw bearing to be advanced toward said outlet when the lead screw is moved distally;
   a drive nut threadedly engaged and screwable along the lead screw threaded shaft;
   a number sleeve threadedly engaged with the housing to be screwable relative to the housing;
   a dial link connected with the drive nut and axially movable and rotatably fixed relative to the drive nut, the dial link rotatably fixed with number sleeve when the dial link and number sleeve are in a first axial arrangement, the number sleeve rotatable relative to the dial link when the dial link and number sleeve are in a second axial arrangement;
   an inner sleeve threadedly engaged with the number, the inner sleeve axially movable and rotatably fixed relative to the housing;
   a mid-body axially fixed inside of the housing, the mid-body comprising tabs that slidably fit within the keyway in the lead screw to prevent rotation of the lead screw within the housing, the mid-body further comprising at least one metal ratchet arm configured to prevent the lead screw from moving in the proximal direction; wherein the inner sleeve is axially movable and rotatably fixed relative to the mid-body by at least one lug of the mid-body that slidably fits within at least one slot formed in the inner sleeve; and wherein the threading of number sleeve to the housing is of a first lead, the threading of the inner sleeve to the number sleeve is of a second lead, and the threading of the lead screw threaded shaft is of a third lead, and the first lead, the second lead and the third lead are not equal;
   wherein during dose setting, the dial link and the number sleeve are in the first axial arrangement, whereby a screwing motion of dial link and number sleeve relative to the housing screws the dial link and the number sleeve a first axial distance from a home position, which screwing motion of dial link screws said drive nut along the lead screw threaded shaft a second axial distance that is different than the first axial distance;
   wherein during dose delivery, the dial link and number sleeve are in said second axial arrangement, whereby a screwing motion of the number sleeve relative to the housing back toward the home position advances the inner sleeve without rotation in the distal direction to axially advance the drive nut that is axially fixed to the inner sleeve and thereby the lead screw and the movable piston to dispense fluid from the cartridge outlet.

2. The drug delivery device as explained in number 1 wherein the metal ratchet arm is molded into the mid-body.

These as well as other advantages of the various aspects of our improved drug delivery device, and the manner of attaining them, will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 1 is an illustration of one embodiment of the present invention showing the assembled pen type medication dispensing apparatus where the cap has been removed to reveal the cartridge container affixed to the dose setting mechanism;

FIG. 2 is a close up-view of the cartridge container and the pen needle that is attached to the cartridge container for injection of the medicament;

Figure 3:
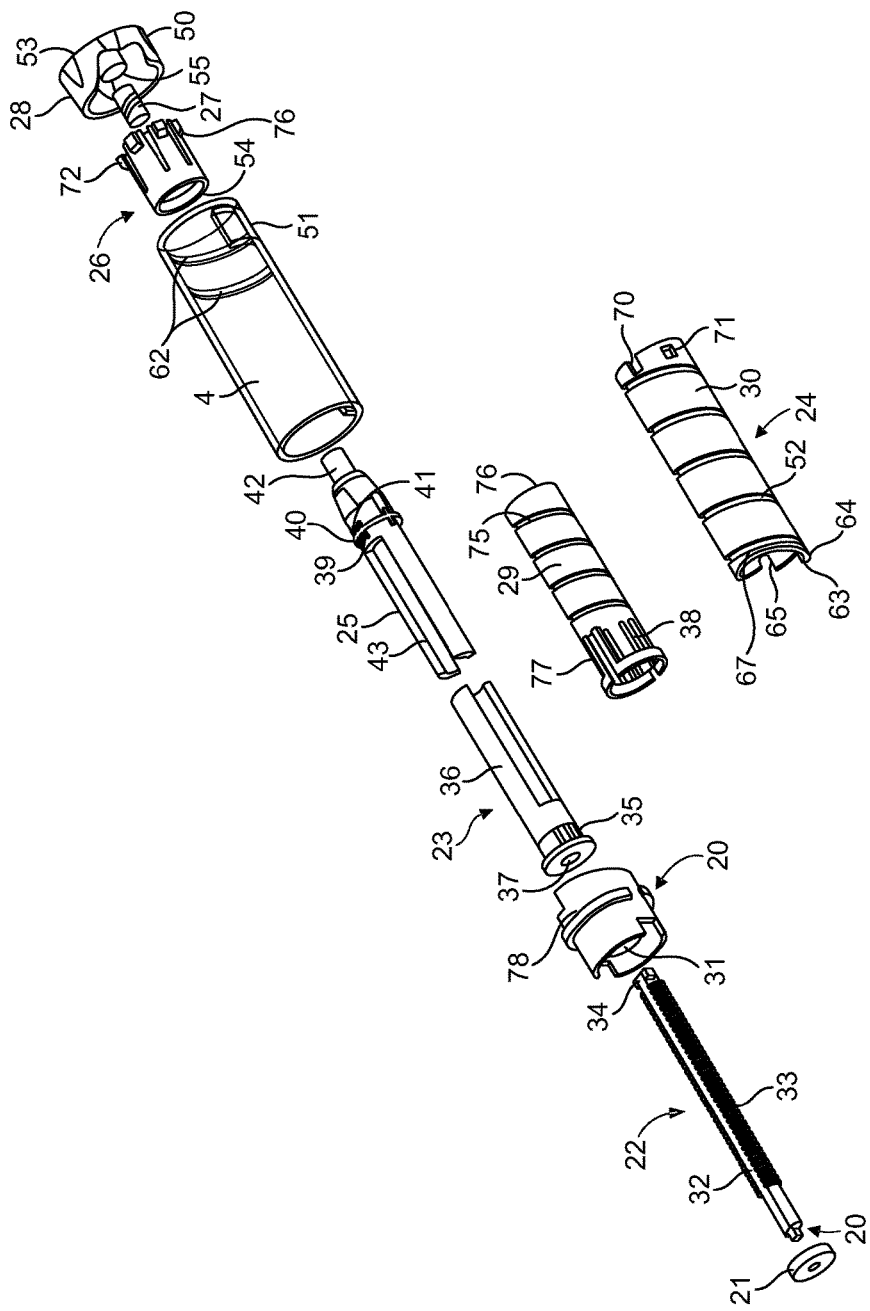
FIG. 3 is an exploded view of the embodiment from FIG. 1 showing each of the individual parts arranged relative to each other as they exist in the fully assembled device.

Corresponding reference characters indicate corresponding parts throughout the several views. Although the drawings represent embodiments of the present invention, the drawings are not necessarily to scale, and certain features may be exaggerated or omitted in some of the drawings in order to better illustrate and explain the present invention.

DETAILED DESCRIPTION

Referring first to FIGS. 1 to 3, there is shown a drug delivery device 1 as an injector pen, which pen has an elongated, substantially writing instrument-like form, although other forms are within the scope of the invention. In other words, the drug delivery device 1 may be a pen-type device. The drug delivery device 1 comprises a housing having a cartridge holder 2, and a main (exterior) body or housing 4.

The drug delivery device 1 and the housing have a distal end and a proximal end. The term "distal end" designates that end of the drug delivery device 1 or a component thereof which is or is to be arranged closest to a dispensing end of the drug delivery device 1. The term "proximal end" designates that end of the device 1 or a component thereof which is or is to be arranged furthest away from the dispensing end of the device 1. The distal end and the proximal end are spaced apart from one another in the direction of an axis. The axis may be the longitudinal axis or rotational axis of the device 1.

The proximal end of the cartridge holder 2 and the distal end of the main housing 4 are secured together by appropriate retaining features depending on whether the pen injector is designed as a reusable device or as a disposable device. In the latter case, the retaining feature would be permanent using the connection means described below. If the device is reusable, the retaining meaning would be a screw type connection, a Luerlok, snap fit, bayonet, or the like type or combination of fittings that allow the user to easily disassemble the device to replace the empty cartridge with a fresh new cartridge. In this illustrated arrangement, the cartridge holder 2 is secured within the proximal end of the main body 4.

A cartridge 8 from which a number of doses of a medicinal product may be dispensed is provided in the cartridge holder 2. Preferably, the cartridge 8 contains a type of medicament that must be administered often, such as once or more times a day. One such medicament is insulin. A piston 10 shown in FIG. 2 is initially retained in the proximal end of the cartridge 8 and as each injection is completed gradually moves distally to the empty cartridge position. A removable cap 14 is releasably retained connected to the main body 4 covering the cartridge holder 2.

The dose setting mechanism of the drug delivery device illustrated in FIGS. 1-3 may be utilized as either for a disposable or reusable drug delivery device. Where the drug delivery device 1 comprises a disposable drug delivery device, the cartridge 8 cannot be removed from the device 1 without destroying the device 1. In a disposable device, the proximal end of the cartridge holder 2 can be fixedly mounted or secured, via adhesives, ultrasonic welding or in another suitable manner, to the dose setting mechanism housing when the injector pen is assembled by the manufacturer. Alternatively, where the drug delivery device 1 comprises a reusable drug delivery device, the cartridge 8 is removable and may be removed from the device 1 without destroying the device 1. In the drug delivery device 1 illustrated in FIGS. 1-3, the device 1 is illustrated as a disposable drug delivery device. However, those of ordinary skill in the art will recognize that the dose setting mechanism could also be used on reusable drug delivery devices as well, while in the case of a reusable pen, wherein the cartridge holder 2 may be reusable, such that the proximal end can be removably mounted or secured, for example via a threaded, bayonet, or snap fit connection, to a reusable dose setting mechanism having a resettable lead screw.

The previously mentioned removable or replaceable cap 14 is used to cover the cartridge holder 2 extending from the main housing 4. Preferably, the outer dimensions of the replaceable cap 14 are similar to or identical to the outer dimensions of the main housing 4 so as to provide an impression of a unitary whole part when the replaceable cap 14 is in position covering the cartridge holder 2. In use, the removable cap 14 is removed and a pen needle assembly 16 comprising a double-ended needle mounted in a hub may be screwed or pushed onto the distal end of the cartridge holder 2 or, alternatively, may be snapped onto this distal end.

Cartridge 8 is of conventional design and defines a medicine-filled reservoir that is closed at its proximal end by the piston 10 that is axially slidably and sealably engaged with the cartridge interior wall to hold the fluid medication within the reservoir. The distal, outlet end of the cartridge reservoir is sealed by a septum 11 held by a cap 13 that is secured to a stepped-down diameter neck portion 15 of the cartridge 8. When the pen needle assembly 16 is mounted on the distal end of the cartridge holder 2, the proximal point of the injection needle passes through a central opening in the distal end of the cartridge holder 2, an opening in the cap 13, and penetrates the cartridge septum 11 to provide a fluid flow outlet by which medicine within the cartridge reservoir can be dispensed from the distal needle tip during operations of injector pen 1. The fluid medicine cartridge 8 shown and described above is illustrative and not intended to be limiting as other constructions may be employed within the scope of this invention.

Main body 4 of injector pen 1 houses an axially advanceable lead screw 22, a drive nut 23, a inner sleeve 29, a dial link 25, a number sleeve 24, a clutch 26, and a compression spring 27. A dose knob 28 is connected to the dial link 25 and is used to set the dose and then to inject the set dose. Housing or main body 4 is formed from a lightweight material, such as injection molded plastic. The housing 4 may be molded as a single, tubular piece for robustness. A window 51 in the housing 4 near its proximal end can be filled with a magnifying lens that snap-fits to the housing 4 and allows dosage indicating markings (not shown) on the number sleeve 24 to be readily visible during use.

Near the interior distal end of the housing 4 is mounted a mid-body 20 that is formed with a central opening having an inward facing anti-rotation mechanism formed from a pair of diametrically opposed elements or tabs 31 having squared off inward ends that each slidably fit within longitudinal keyways 32 in the lead screw 22. In alternate embodiments, features other than tabs and keyways, for instance a lead screw with flats that fits within a complementarily shaped hole in a collar, may be used to prevent rotation. The tabs 31 prevent the lead screw 22 from rotating within the housing 4 during pen use, but permit the lead screw 22 to be shifted longitudinally, such as in the distal direction towards the cartridge 8. A snap fit or sonic welding connection of the mid-body 20 to the tubular housing 4 can be used to prevent axial and rotational relative motion of the mid-body 20 to the housing 4.

The lead screw 22 is in the form of a screw that is axially translatable and rotatably fixed during dosing and injecting. The term "rotatably fixed" shall mean in this context that the lead screw 22 is prevented from rotation during dosing and injecting. The lead screw 22 includes a shaft with a helical threading 33 along its length, which threading 33 is interrupted by the longitudinally extending keyways or grooves 32. A thread stop 34 shown at the proximal end of the threading 33 is provided and is used in preventing the pen from being set by a user to deliver a dose of medicine larger than remains in cartridge 8. Other forms of stopping the screw motion may be substituted within the scope of the invention, for example, the threading at the proximal screw end could stop near the proximal end where it can not be cammed in, and such solid screw with thread stop better ensures the nut 23 will not be torqued off the screw during dose setting. The distal end of lead screw 22 includes an enlarged, disc-shaped foot or bearing 21 to distribute loading on the cartridge piston 10 that the bearing 21 contacts and thereby directly engages during the piston 10 advancing. The separate bearing foot 21 can be attached, such as with a snap fit 20 that may permit relative rotation, to the lead screw 22. The lead screw 22 is shown as being a one-piece plastic injection molding, but alternate materials of construction and multiple pieces are possible.

Figure 4:
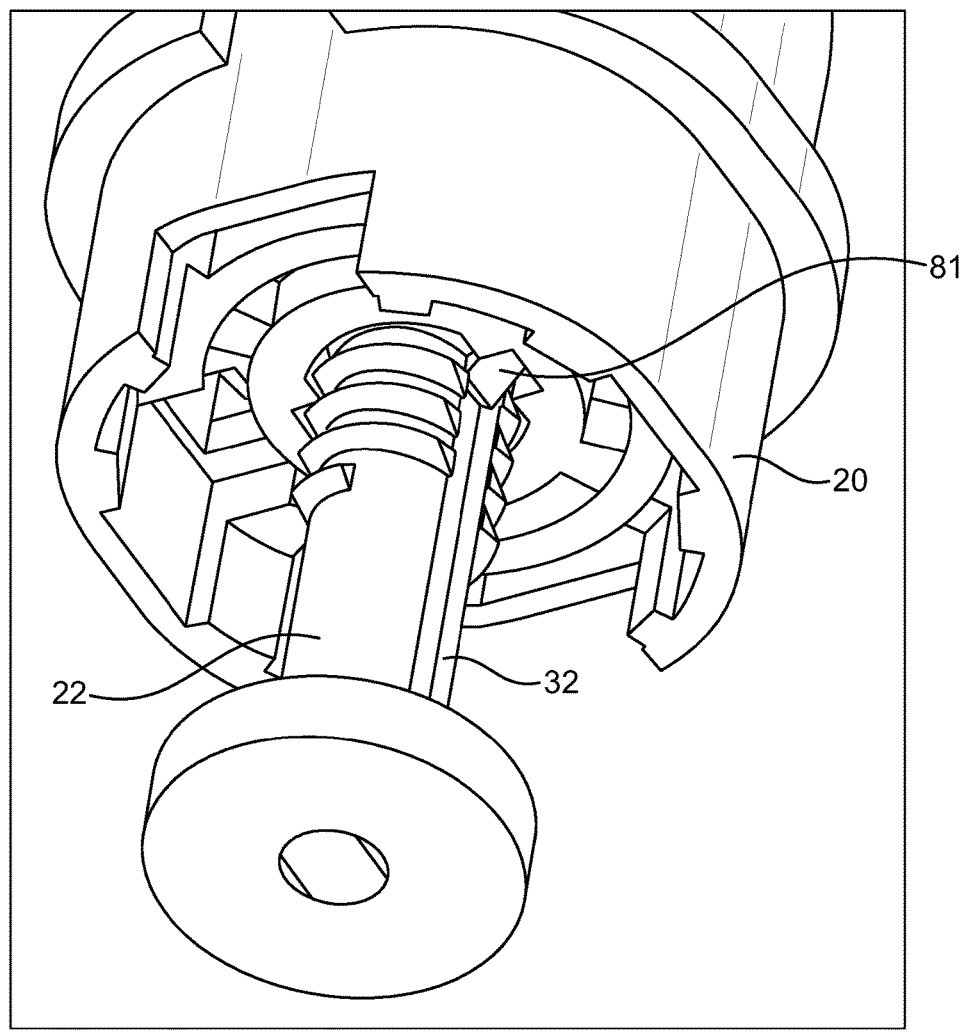
FIG. 4 is a perspective view of one embodiment of the modified mid-body configuration.
Figure 5:
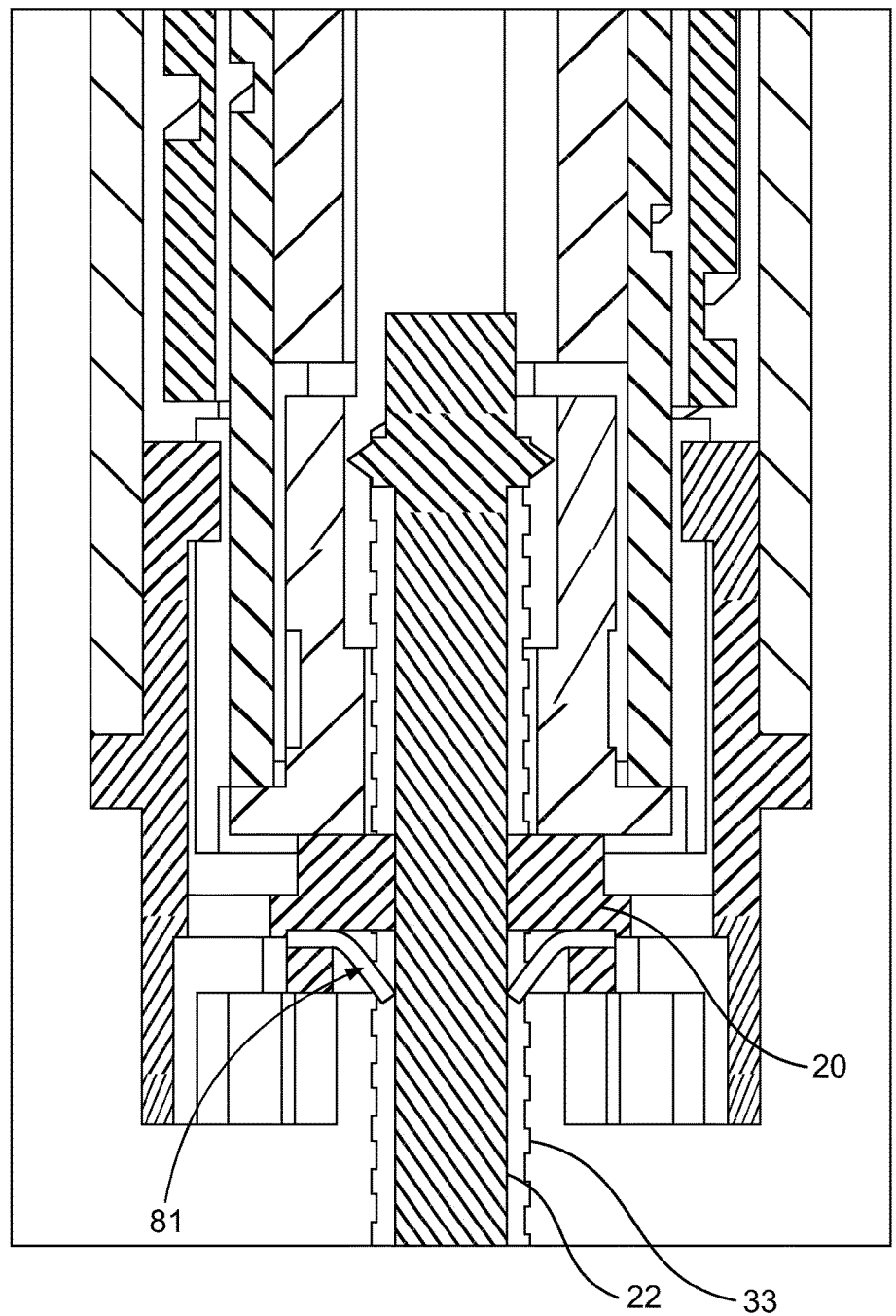
FIG. 5 is a cross-sectional view of the embodiment illustrated in FIG. 4.

FIG. 4 illustrates a close-up view of the mid body 20 and the lead screw 22 configuration providing an anti-backup feature. The keyway 32 configuration comprises a smooth surface that is engaged by a metal ratchet arm 81. FIG. 5 is a cross-sectional view of the embodiment illustrated in FIG. 4.

As shown in FIG. 5, the ratchet arm 81 has an angled or wedge shaped distal end that claws or "digs into" the smooth surface of the keyway 22. In this position, the metal ratchet arm 81 prevents the lead screw 22 from moving in the proximal direction, such as during the situation described above. Preferably, one or more metal ratchet arms 81 may be provided. In one preferred arrangement, the metal ratchet arm 81 may comprise a separate metal spring. In an alternative arrangement, the metal ratchet arm 81 may be molded into the mid body 20. Alternatively, the ratchet arm 81 may also be of plastic material or other synthetic material.

The drive nut 23 includes a cylindrical, tube-shaped body with flexible fingers 36 and clicker teeth 35. The distal region of the drive nut 23 is formed with an internal threading 37 that threadedly engages in a friction locking fashion the threading 33 on the lead screw 22. Threadings 33 and 37 are shown as a double start threading but may be differently formed while still providing suitable friction locking capabilities, such as a single start threading or another multiple start threading. The drive nut 23 is located within the inner sleeve 29 and is axially, but not rotationally fixed, to the inner sleeve 29. As the drive nut 23 is rotated relative to inner sleeve 29 during dose setting, the clicker teeth 35 engage in a ratchet fashion flexible arms 38 that project radially on the inside of the inner sleeve 29. As the drive nut 23 rotates, the flexible arms 38 ride over the teeth 35 creating an audible clicking noise. The teeth 35 are configured so that each click is equal to one dose volume being set. As few as one flexible clicker arm 38 may be provided, but the use of four equally angularly spaced arms 38 aids in centering the drive nut 23 within the inner sleeve 29. The hollow interior of the drive nut body 23 located proximally of the threading 37 allows free passage of the proximal end of the lead screw 22. The exterior surface of the drive nut 23 is designed to cooperatively engage with the dial link 25 so that the dial link 25 is axially free and rotatably fixed relative to the drive nut 23. Thus, during use the dial link 25 is axially moveable relative to, but rotatably locked with, the threaded drive nut 23. This connection is possible because of the cooperation of the proximally extending fingers 36 on the drive nut 23 and the distally extending fingers 43 of the dial link 25. These two sets of fingers 36, 43 move axially relative to each other but engage each other rotationally during dose setting when the dial link 25 is rotated by turning the dose knob 28, which is fixed to the dial link 25. The drive nut 23 is shown as being a one-piece plastic injection molding, but other constructions are within the scope of the invention.

In the shown embodiment, the dial link 25 is formed in one piece of an injection molded plastic and which fits within the body 4. A flange 40 that rings a central region of the dial link body includes splines or teeth 39 that extend from the distal face of the flange 40, and teeth 41 that extend from the proximal face of the flange 40. A stepped-down portion of the proximal end of the dial link 25 forms an axially and proximally extending stem 42. The distal end of the dial link body includes the pair of fingers 43 that fit with the fingers 36 of the drive nut 23 to allow axial motion but not rotational motion of the drive nut 23 relative to the dial link 25, thereby rotationally locking the pieces together within the same annular space. Fingers 36 and 43 extend sufficiently axially to ensure they do not disengage during the setting of the maximum pen dose for injection.

An injection molded plastic dose knob 28 with a proximal face, and having a distally facing and centrally located bearing collar and alignment post 55 is provided. The stem 42 of the of the dial link 25 receives the dose knob alignment post and can be ultrasonically welded within the bearing collar during manufacturing assembly, so as to axially and rotatably fix together the dose knob 28 and the dial link 25. The term "rotatably fix" shall mean in this context that any relative rotational movement between the dose knob 28 and the dial link 25 is prevented. A dose knob skirt 50 distally extends from the radial periphery of the dose knob distal face to serve as a grip portion for a user during dose setting.

Coaxially mounted around the dial link 25 is the number sleeve 24. The number sleeve 24 has a cylindrical exterior surface 30 with a threading 52 formed as a helical groove that engages a corresponding threading 62 formed on the interior surface of body 4 to threadedly engage the number sleeve 24 to the pen housing. Threadings 52 and 62 are shown as a single start threading but may be differently formed. Threading 62 abuts an end 63 of the threading 52 on the number sleeve 24 at the maximum pen dose, assuming the cartridge 8 is sufficiently full for such a maximum dose. A stop surface 64 on the distal end of the outer surface of the number sleeve 24 is positioned in slightly spaced apart relationship with a projecting stop at the zero dose position, and another stop surface is to be abutted by the stop if a user attempts to manually screw the screw element below a zero dose position. A hollow interior 65 of the number sleeve 24 is defined by a cylindrical interior surface provided with a helical threading 67.

The outside diameter of the number sleeve 24 is selected such that it can fit inside the dose knob 28. The proximal end region of number sleeve 24 includes a number of notches 70 and corresponding windows 71 that are alternately spaced around the circumference. The number sleeve 24 includes around its exterior surface 30 suitable indicia of therapeutic dose size as visible through body 4 opening 51. A clutch 26 fits within the open proximal end of the number sleeve 24. Ears 72 on the clutch 26 fit within notches 70 and assembly fingers 73 snap-lock into windows 71 to axially and rotatably lock the number sleeve 24 and the clutch 26 together during manufacturing assembly. A ring of axially extending teeth 54 on the clutch 26 formed in the interior surface of a flange cooperate with the dial link teeth 41 proximally facing on dial link 25.

Disposed between the clutch 26 and the inside portion of the dose knob 28 is the compression or biasing spring 27 that urges the clutch 26 to engage the teeth 41 on the dial link 25. During injection, when a user manually applies a plunging force onto the proximal face of the dose knob 28, the spring 27 is elastically compressed, thus disengaging the clutch 26 and number sleeve 24 from the dial link 25. Flange teeth 41 on the dial link 25 and clutch teeth 54 mesh when the spring 27 has biased the clutch 26 and attached the number sleeve 24 to the dose knob 28 and dial link 25. Dose knob 28 and dial link 25 are not meshed with the clutch 26 and number sleeve 24 when the spring 27 has been sufficiently compressed during injecting. While a helically coiled metal wire spring is shown, other forms of commonly known biasing elements may be substituted.

The inner sleeve 29 is injection molded from plastic and includes a tubular body that fits into the hollow 65 of the number sleeve 24. The inner sleeve 29 has a helical threading 75 on its outer surface that engages the internal threading 67 on the inside surface of the number sleeve 24. Threadings 67 and 75 are shown as a single start threading, but may be differently formed. The proximal most portion of the end of inner sleeve 24, which end is partially helically shaped corresponding to the threading, is notched to form a partial ring of axially projecting teeth 76 that, when meshed with dial link distally facing teeth 39, serve to rotatably lock together the dial link 25 and the inner sleeve 29. Inner sleeve 29 is keyed to pen body 4 through an intermediate mid-body 20 that is axially and rotationally fixed to the body 4. The distal end of inner sleeve 29 has a pair of ridge-defined slots 77 on the periphery of the inner sleeve 29 which axially, slidably receive lugs 78 radially inwardly projecting from the mid-body 20.

Openings molded into inner sleeve 29 define four resilient fingers 38 having radially inwardly projecting teeth that are axially oriented and shaped to project into a recess in the distal end of drive nut 23 that has radially projecting teeth or ridges 35 such that the inwardly projecting teeth click over, in either rotational direction, teeth 35 during dose setting. The fingers 38 with teeth cooperate with the recess on the drive nut 23 to hinder the nut 23 from coming off the inner sleeve 29 after being assembled thereto during manufacture.

To facilitate back-driving during dose delivery, the threaded connections of the number sleeve 24 and the body 4, and the number sleeve 24 and the inner sleeve 29, are non-binding and provided by projecting 60° face angle threads that slide within correspondingly designed recessed grooves. With these threadings, it is preferred that the mechanical advantage is 3.4 or greater, and the screw lead of the drive member or drive nut 23 is 0.108 inch.

The operation of the above described embodiment will now be explained. The pen 1 with a needle 16 attached should first be primed to remove any trap air in the cartridge 8 and to ensure the bearing 21 is in contact with the proximal end of the cartridge stopper or piston 10. In particular, typically while clutching the pen body 4 in one hand, a user manually grips the dose knob skirt 50 and then begins to turn the knob 28 relative to the body 4. At the zero dose arrangement, and as long as knob 28 is not also being plunged which is improper, knob 28 can only be rotated in a dose increasing direction due to the number sleeve 24 not being further movable distally. A user stops the rotating after a short amount of number sleeve 24 travel that is associated with a small delivery volume, such as one or two units, which is indicated by the markings visible through a window 51. Then, and after removing the cap 14 and any other needle cap present, and while pointing the needle tip upward, the user applies a plunging force on dose knob 28 to drive it distally until the number sleeve 24 returns to the zero dose position, at which the number sleeve threading 52 has reached the distal end of the body threading 62, during which plunging action the piston 10 is shifted forward within cartridge 8. If a user sees that the piston movement has caused liquid to reach the needle distal tip, the priming process is complete. If no liquid is visible at the needle tip, the priming steps are repeated as needed. After priming, the pen 1 is ready to be used for an actual injection.

First, a user prepares the pen by setting the desired dose, as visible in the window 51, by turning of the knob 28. If the user dials up too large of a dose, and without expelling any medicine, the user can rotate down the dial by turning the knob 28 in the opposite direction, all the way back to zero if desired. To set a dose, the knob 28 is turned in a clockwise direction. Because the dose knob 28 and dial link 25 are fixed rotationally, the dial link 25 is rotated causing the distally facing fingers 43 to engage the proximally facing fingers 36 of the drive nut 23 to thereby turn the drive nut 23 in same direction. Rotation of the drive nut 23 causes the nut 23 to rotate relative to the stationary lead screw 22 whereby the nut 23 moves or climbs up the lead screw 22 in the proximal direction. The drive nut 23 rotates relative to the inner sleeve 29 that is held rotationally fixed relative to the body 4 through the splined connection to the mid-body 20. Because the drive nut 23 and inner sleeve 29 are axially fixed, proximal axial movement of the drive nut 23 causes the inner sleeve 29 to slide proximally relative to the mid-body 20. Because the clutch 26 is rotationally fixed with the dial link 25 the clutch 26 rotates causing the number sleeve 24 to rotate and to spin out proximally away from body 4. Because the pitch of the threads on the number sleeve 24 are greater than the pitch of the threads on the inner sleeve 29, the number sleeve 24 and the dial link 25 will translate a larger axial distance as compared to the inner sleeve 29 and the drive nut 23.

To inject the dose, after pen 1 is manipulated so the injection needle distal tip properly penetrates, for example, a user's skin, an axial, distal plunging force is applied to knob face 53 to force the dial link 25 axially in the distal direction towards the body 4, such as with a thumb or index finger of the hand which grasps the housing 4. Initially during injecting, the dial link 25 is shifted axially, which shifting motion compresses the biasing spring 27 to close the gap between the knob surface and the proximal end of the number sleeve 24. The biasing spring 27 is designed to compress prior to the number sleeve 24 moving relative to the body 4. When dial link 25 shifts relative to the number sleeve 24 to the axial arrangement of the drive nut 23, the clutch teeth 54 and dial link teeth 42 disengage to allow a backdriving rotation of the number sleeve 24 relative to the dial link 25. During the axial movement of the dial link 25, drive nut 23 does not move axially or rotationally. When the number sleeve 24 and clutch 26 rotatably uncouple from the dial link 25, as the dial link 25 is continued to be axially plunged without rotation by the user by the plunging of knob 28, the number sleeve 24 screws into the body 4 as it spins relative to knob 28 and the dose markings on the number sleeve 24 that indicate the amount still remaining to be injected are visible through the window 51.

As it screws down, number sleeve 24 causes inner sleeve 29 to in essence screw up the internal thread inside of the number sleeve threading as the inner sleeve 29 advances distally a lesser distance than the number sleeve 24. The advancement of the inner sleeve 29, due to the abutting or direct engagement with the distal end of the drive nut 23, advances drive nut 23 without rotation, which due to its threaded connection with the lead screw 22 advances the lead screw 22 axially without rotation, which lead screw advancement shifts cartridge piston 10 to expel medication from the cartridge reservoir. The injection is completed when the number sleeve threading 52 has reached the distal end of the body 4, at which time pen 1 is once again arranged in the ready state or zero dose position.

Pen 1 can continue to be used to deliver any desired dose until the medicine remaining in the cartridge 8 is insufficient for a proper dosing. This insufficiency is indicated to the user by the inability to fully set the desired dose due to drive nut threading 37 abutting thread stop 34 of the lead screw 22, at which time the drive nut 23 and dial link 25 cannot be rotated proximally any farther. When insufficient medicine remains, pen 1 is to be disposed of and replaced with a similar but entirely new pen.

The terms "medicament" or "medicinal product", as used herein, mean a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys) 6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the aforementioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ, and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

While this invention has been shown and described as having various designs, the present invention may be modified within the spirit and scope of this disclosure. For example, to deliver a fixed dose, the pen would preferably be modified such that the maximum that the dial could be screwed out to prepare the pen for injection would correspond to the fixed dose. Such a fixed dose pen could eliminate numerical dosage indicating marking, and instead provide user cues in the form of, for example, instructions and a graphical dosing indicator. This application is therefore intended to cover any variations, uses or adaptations of the invention using its general principles. Further, this application is intended to cover such departures from the present disclosure as come within known or customary practice in the art to which this invention pertains.

The invention claimed is:

1. A drive assembly for a drug delivery device, the drive assembly comprising:
   a housing;
   a piston rod having a longitudinal axis, a distal end, and a proximal end, the piston rod being axially movable in a distal direction relative to the housing;
   a mid-body axially fixed inside of the housing and coupled to the piston rod; and
   at least two metal ratchet arms, each of the at least two metal ratchet arms comprising
      a respective connecting portion attached to the mid-body, and
      a respective distal end extending distally relative to the respective connecting portion and inwardly toward the longitudinal axis,
   wherein the piston rod has at least one keyway with a smooth surface positioned parallel to the longitudinal axis, the at least two metal ratchet arms being guided in the at least one keyway of the piston rod and engaging the smooth surface of the at least one keyway of the piston rod, and
   wherein the at least two metal ratchet arms are configured to prevent the piston rod from moving in a proximal direction relative to the housing by digging into the smooth surface of the at least one keyway of the piston rod.

2. The drive assembly according to claim 1, wherein the at least two metal ratchet arms are molded into the mid-body, the mid-body being fabricated from plastic or other synthetic material.

3. The drive assembly according to claim 1, wherein each of the at least two metal ratchet arms has a respective angled or wedge shaped end section pointing in the distal direction and contacting a surface of the piston rod.

4. The drive assembly according to claim 1, wherein the mid-body comprises tabs that slidably fit within the at least one keyway of the piston rod to prevent rotation of the piston rod within the housing.

5. The drive assembly according to claim 4, wherein the tabs are distinct from the at least two metal ratchet arms.

6. The drive assembly according to claim 1, wherein the piston rod is formed as a lead screw that is rotatably fixed during dose setting and dose delivery, the lead screw including a threaded shaft and a bearing foot connected to the distal end of the piston rod.

7. The drive assembly according to claim 6, further comprising a drive nut threadedly engaged and screwable along the threaded shaft of the lead screw.

8. The drive assembly according to claim 7, further comprising a number sleeve threadedly engaged with the housing to be screwable relative to the housing.

9. The drive assembly according to claim 8, further comprising a dial link connected with the drive nut and axially movable and rotatably fixed relative to the drive nut, the dial link rotatably fixed with the number sleeve when the dial link and the number sleeve are in a first axial arrangement, the number sleeve being rotatable relative to the dial link when the dial link and the number sleeve are in a second axial arrangement.

10. The drive assembly according to claim 9, further comprising an inner sleeve threadedly engaged with the number sleeve, the inner sleeve being axially movable and rotatably fixed relative to the housing, wherein the inner sleeve is axially movable and rotatably fixed relative to the mid-body by at least one lug of the mid-body that slidably fits within at least one slot formed in the inner sleeve.

11. The drive assembly according to claim 10, wherein a threading of the number sleeve to the housing is of a first lead, a threading of the inner sleeve to the number sleeve is of a second lead, and a threading of the threaded shaft is of a third lead, whereby the first lead, the second lead, and the third lead are different from one another.

12. The drive assembly according to claim 11, wherein during dose setting, the dial link and the number sleeve are in the first axial arrangement, whereby a screwing motion of the dial link and the number sleeve relative to the housing screws the dial link and the number sleeve a first axial distance from a home position, the screwing motion of the dial link screwing the drive nut along the threaded shaft a second axial distance that is different from the first axial distance, and
   wherein during dose delivery, the dial link and the number sleeve are in the second axial arrangement, whereby a screwing motion of the number sleeve relative to the housing back toward the home position advances the inner sleeve without rotation in the distal direction to axially advance the drive nut that is axially fixed to the inner sleeve and thereby the lead screw.

13. The drive assembly according to claim 1, wherein the respective connecting portion of each of the at least two metal ratchet arms extends inwardly from the mid-body toward the longitudinal axis, and the respective distal end of each of the at least two metal ratchet arms extends distally and inwardly from a respective inwardmost portion of the respective connecting portion.

14. A drug delivery device with a drive assembly according to claim 1, further comprising a cartridge with a movable piston at one end and an outlet at the other end, the piston engagable by the distal end of the piston rod to be advanced toward the outlet when the piston rod is moved distally so as to dispense fluid from the outlet.

15. A drive assembly for a drug delivery device, the drive assembly comprising:

a housing;

a piston rod having a longitudinal axis, a distal end, and a proximal end, the piston rod being axially movable in a distal direction relative to the housing;

a mid-body axially fixed inside of the housing and coupled to the piston rod; and at least two metal ratchet arms, each of the at least two metal ratchet arms comprising a respective connecting portion attached to the mid-body, and a respective distal end extending distally relative to the respective connecting portion and inwardly toward the longitudinal axis, wherein the piston rod is a lead screw comprising a thread, wherein the at least two metal ratchet arms do not engage the thread of the lead screw.

16. A drive assembly for a drug delivery device, the drive assembly comprising:

a housing;

a piston rod having a longitudinal axis, a distal end, and a proximal end, the piston rod being axially movable in a distal direction relative to the housing; and a mid-body axially fixed inside of the housing and coupled to the piston rod; and at least one metal ratchet arm comprising a connecting portion attached to the mid-body, and an angled or wedge shaped distal end extending relative to the connecting portion of the at least one metal ratchet arm and inwardly toward the longitudinal axis, the angled or wedge shaped distal end pointing in the distal direction and contacting a surface of the piston rod, wherein the piston rod has a keyway with a smooth surface positioned parallel to the longitudinal axis, the at least one metal ratchet arm being guided in the keyway of the piston rod and engaging the smooth surface of the keyway of the piston rod, and wherein the at least one metal ratchet arm is configured to prevent the piston rod from moving in a proximal direction relative to the housing by digging into the smooth surface of the keyway of the piston rod.

* * * * *